(12) United States Patent
Takai et al.

(10) Patent No.: US 6,770,795 B2
(45) Date of Patent: Aug. 3, 2004

(54) DISPOSABLE BODY FLUID ABSORBENT WEARING ARTICLE

(75) Inventors: Hisashi Takai, Kagawa-ken (JP); Koichi Yamaki, Kagawa-ken (JP); Miou Suzuki, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 340 days.

(21) Appl. No.: 09/940,930

(22) Filed: Aug. 28, 2001

(65) Prior Publication Data

US 2002/0026169 A1 Feb. 28, 2002

(30) Foreign Application Priority Data

Aug. 28, 2000 (JP) ........................................ 2000-257639

(51) Int. Cl.[7] .......................... A61F 13/15; A61F 13/20
(52) U.S. Cl. ..................................... 604/378; 604/380
(58) Field of Search ........................... 604/378, 385.01, 604/379, 380, 367

(56) References Cited

U.S. PATENT DOCUMENTS

| | | | | |
|---|---|---|---|---|
| 5,395,359 A | * | 3/1995 | Nakanishi et al. | 604/378 |
| 5,865,822 A | * | 2/1999 | Hamajima et al. | 604/367 |
| 6,068,619 A | * | 5/2000 | Hamajima et al. | 604/378 |

* cited by examiner

*Primary Examiner*—John J. Calvert
*Assistant Examiner*—Michele Kidwell
(74) *Attorney, Agent, or Firm*—Butzel Long

(57) ABSTRACT

A disposable body fluid absorbent wearing article includes a liquid-pervious topsheet including plastic film layer sections, liquid-pervious openings and a first fibrous layer bonded to the lower surface of the film layer sections. A second fibrous layer forming a liquid-absorbent core is contiguous to the lower surface of a first fibrous layer and a third fibrous layer is contiguous to the lower surface of the second fibrous layer. The wearing article is constructed so that its Klemm's water absorbency may progressively increase in the order of the first fibrous layer, the second fibrous layer and the third fibrous layer.

10 Claims, 8 Drawing Sheets

DISPOSABLE BODY FLUID ABSORBENT WEARING ARTICLE

BACKGROUND OF THE INVENTION

This invention relates to a disposable body fluid absorbent wearing article such as a disposable diaper, an urine absorbent pad or a sanitary napkin.

Figure 9:
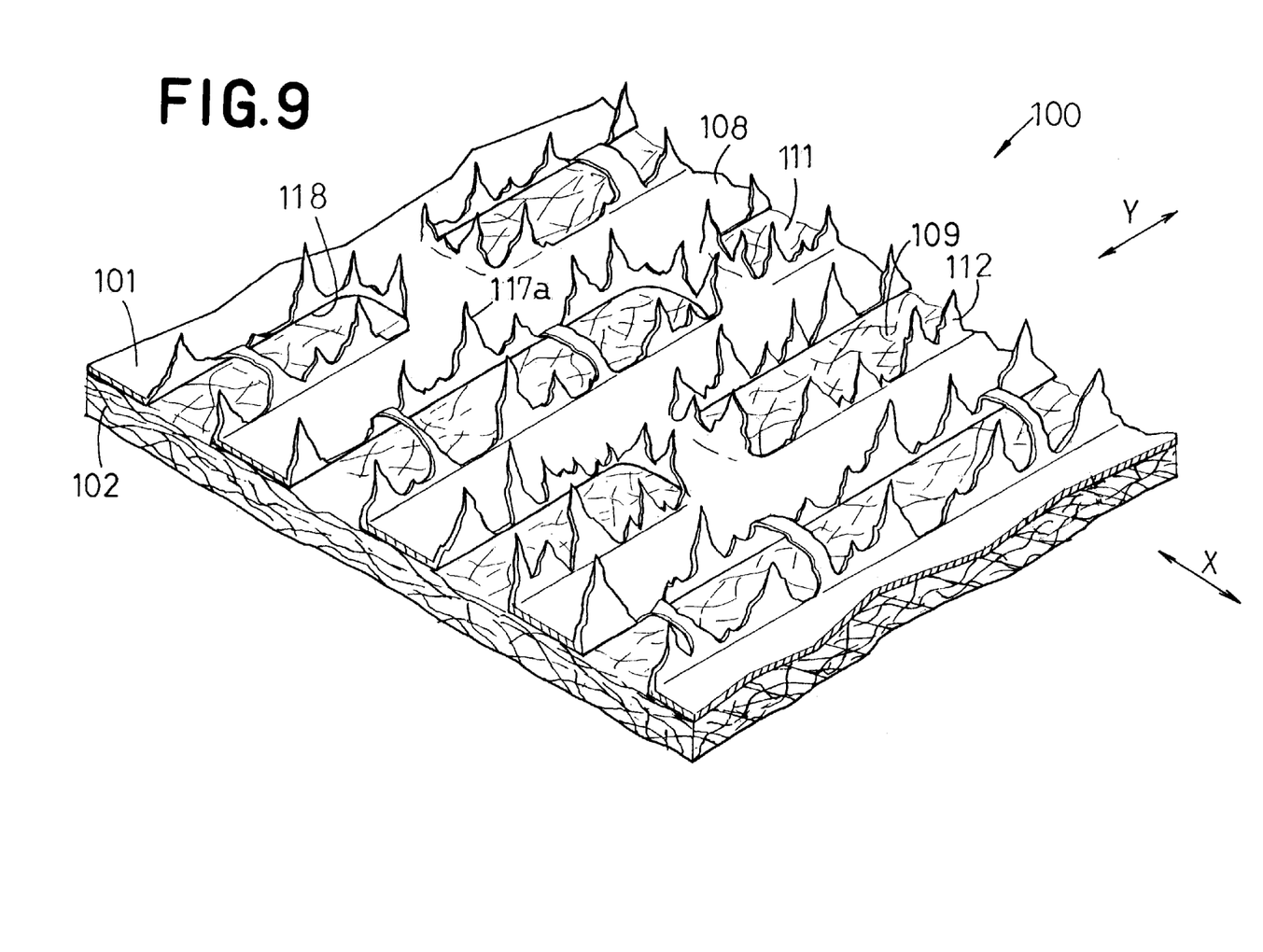
FIG. 9 is a perspective view showing a topsheet of prior art.

FIG. 9 of the accompanying drawings is a perspective view showing a liquid-pervious flexible composite sheet 100 described in Japanese Patent Application Publication No. 1999-217453A. This composite sheet 100 is adapted to be used as a liquid-pervious topsheet covering a liquid-absorbent core in a body fluid absorbent wearing article. The composite sheet 100 comprises a plastic sheet 101 and a fibrous layer 102 bonded to the lower surface of the sheet 101. The sheet 101 has a plurality of flat zones 108 extending in parallel one to another in Y-direction and a plurality of opening arrays 111 extending in the Y-direction, each of the arrays comprising a plurality of openings 109. Each of the flat zones 108 are formed along its edges 118 with rising portion 112 extending upward from the flat zone 108. Upper edge 117a of the rising portion 112 undulates along the edges 118. In the case of the disposable diaper using this composite sheet 100 as its liquid-pervious topsheet, a quantity of body fluids discharged on the flat zones 108 of the composite sheet 100 will flow through the troughs defined between respective pairs of the adjacent individual rising portions 112, 112 into the openings 109 and then will be absorbed by the core underlying the composite sheet 100. The plastic sheet 101 has its initial shape held by the fibrous layer 102 and therefore it is not apprehended that the sheet 101 might be wrinkled and consequently a plurality of the openings 109 might be substantially closed. The composite sheet 100 preferably has a breathability of 5~700 cm$^3$/cm$^2$·sec as measured in accordance with prescription of JIS L 1096 and a water-resistance of 0~200 mm as measured in accordance with prescription of JIS L 1092.

The flexible composite sheet of prior art is certainly advantageous in that a plurality of projections, i.e., individual rising portions serve to offer a cloth-like touch in spite of being made from plastic sheet material and a plurality of openings serve to improve the liquid- and air-permeability. In addition, this composite sheet is hydrophobic in its flat zones as well as in its rising portion so that a cloth-like touch free from wetness may be maintained even after body fluids have been discharged thereon. However, these flat zones and rising portion are rather repellent against body fluids and may deteriorate the desired liquid-permeability of the composite sheet.

SUMMARY OF THE INVENTION

It is an object of this invention to provide a disposable body fluid absorbent wearing article that maintains a dried cloth-like touch and the high liquid-permeability.

According to this invention, there is provided a disposable body fluid absorbent wearing article comprising a liquid-pervious topsheet, a liquid-impervious backsheet and a liquid-absorbent core disposed between these top- and backsheets.

According to this invention the topsheet comprises plastic film layer sections each having upper and lower surfaces and a thickness of 0.001~0.05 mm, liquid-pervious openings defined between respective pairs of the adjacent plastic film layer sections and a first fibrous layer bonded to the lower surfaces of the plastic film layer sections and immediately underlying the openings, the topsheet having a Klemm's water absorbency lower than 10 mm, each of the openings has a width of 0.05~1 mm so that a total open area thereof occupies 3~40% of a surface area of the topsheet, edges of the plastic film layer sections defining the openings being partially fibrillated so as to form a rising portion having the maximum height of 1.5 mm and component fibers of the first fibrous layer having a fineness of 0.5~20 dtex and a basis weight of 5~60 g/m$^2$; and the core has a second fibrous layer being closely contiguous to the lower surface of the first fibrous layer and a third fibrous layer being closely contiguous to the lower surface of the second fibrous layer wherein the second fibrous layer has a Klemm's water absorbency is lower than 35 mm but higher than a Klemm's water absorbency of the topsheet by 15 mm or more and the third fibrous layer has a Klemm's water absorbency of at least 35 mm but higher than the Klemms water absorbency of the second fibrous layer by 15 mm or more.

DETAILED DESCRIPTION OF THE PREFERRED EMBODIMENTS

Details of a disposable body fluid absorbent wearing article will be more fully understood from the description given hereunder with reference to the accompanying drawings in which typical and several preferred embodiments in the form of sanitary napkin are shown.

Figure 1:
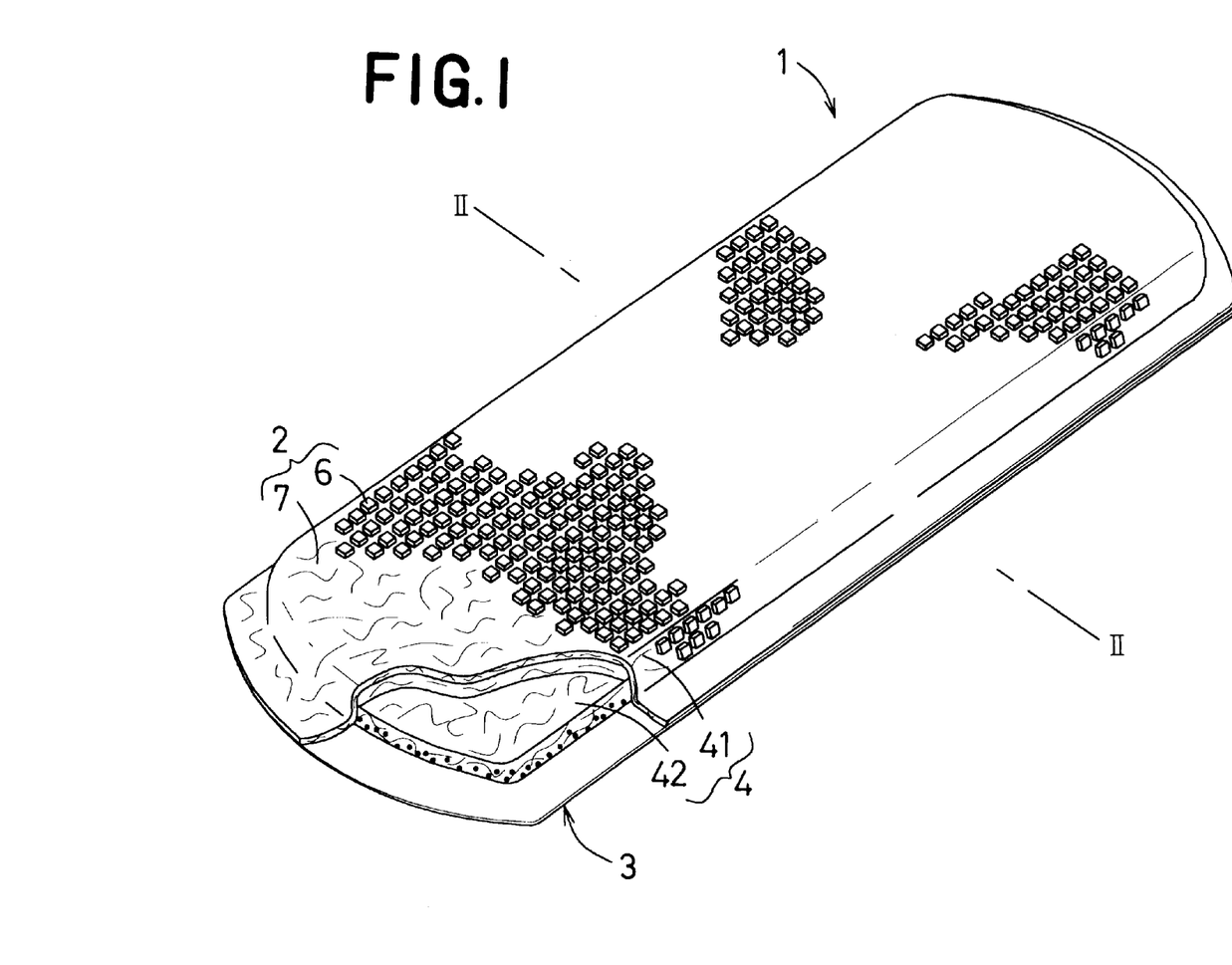
FIG. 1 is a perspective view showing a disposable body fluid absorbent wearing article according to this invention (in the form of sanitary napkin) as partially broken away.

A sanitary napkin 1 shown by FIG. 1 in a perspective view as partially broken away comprises a liquid-pervious topsheet 2, a liquid-impervious backsheet 3 and a liquid-absorbent core 4 disposed between these top- and backsheets 2, 3. The portions of these top- and backsheets 2, 3 extending outward laterally beyond transverse opposite side edges of the core 4 are put flat under a pressure and bonded or welded together. The topsheet 2 has a plurality of flat plastic film layer sections 6 lying on the body side of a wearer and a fibrous assembly layer 7 bonded to the lower surfaces of the film layer sections 6. The core 4 has a concealing layer 41 bonded to the lower surface of the fibrous assembly layer 7 and a liquid holding layer 42 bonded to the lower surface of the concealing layer 41. The backsheet 3 comprises a single plastic sheet.

Figure 2:
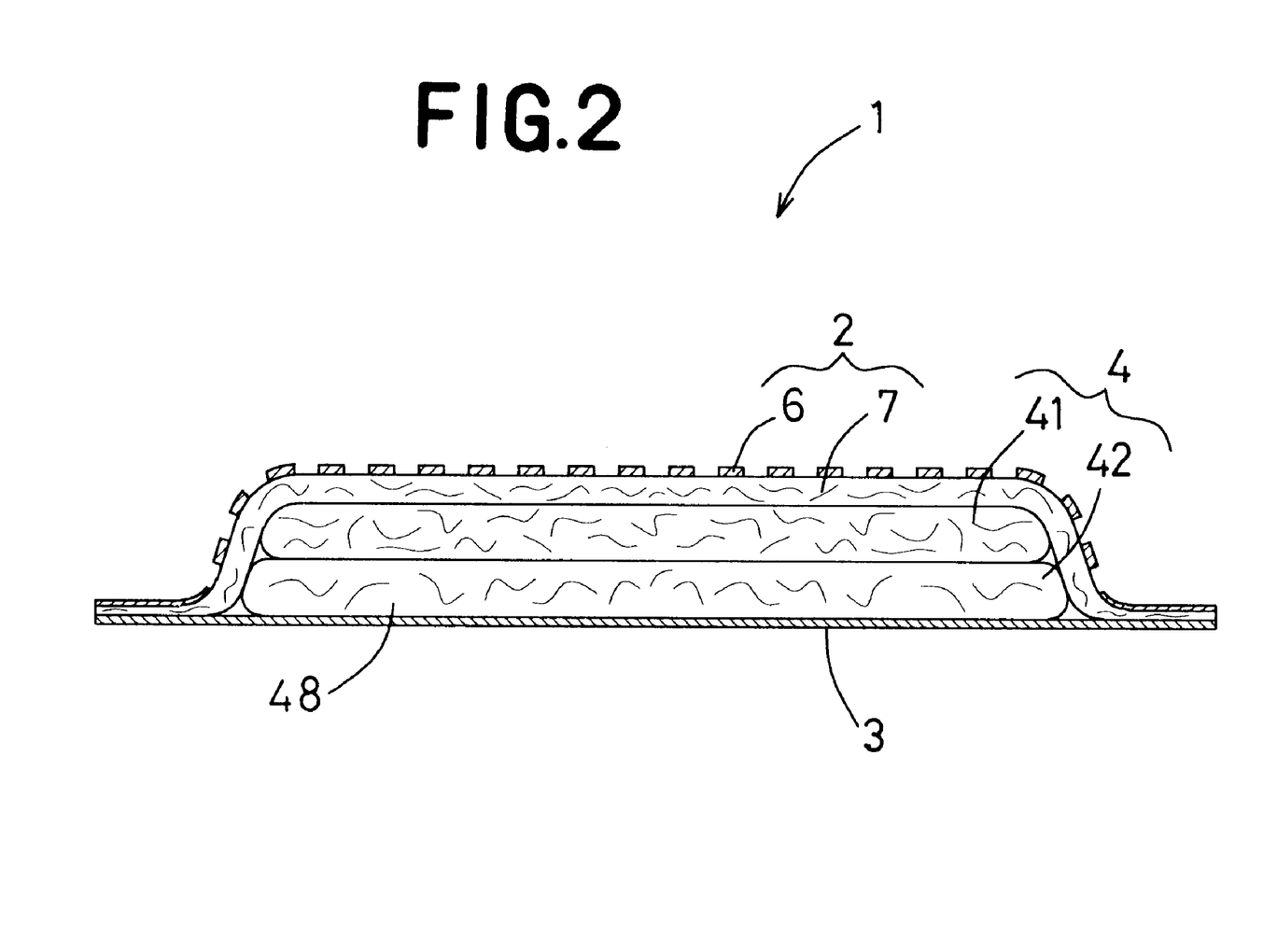
FIG. 2 is a sectional view taken along a line II—II in FIG. 1.
Figure 3:
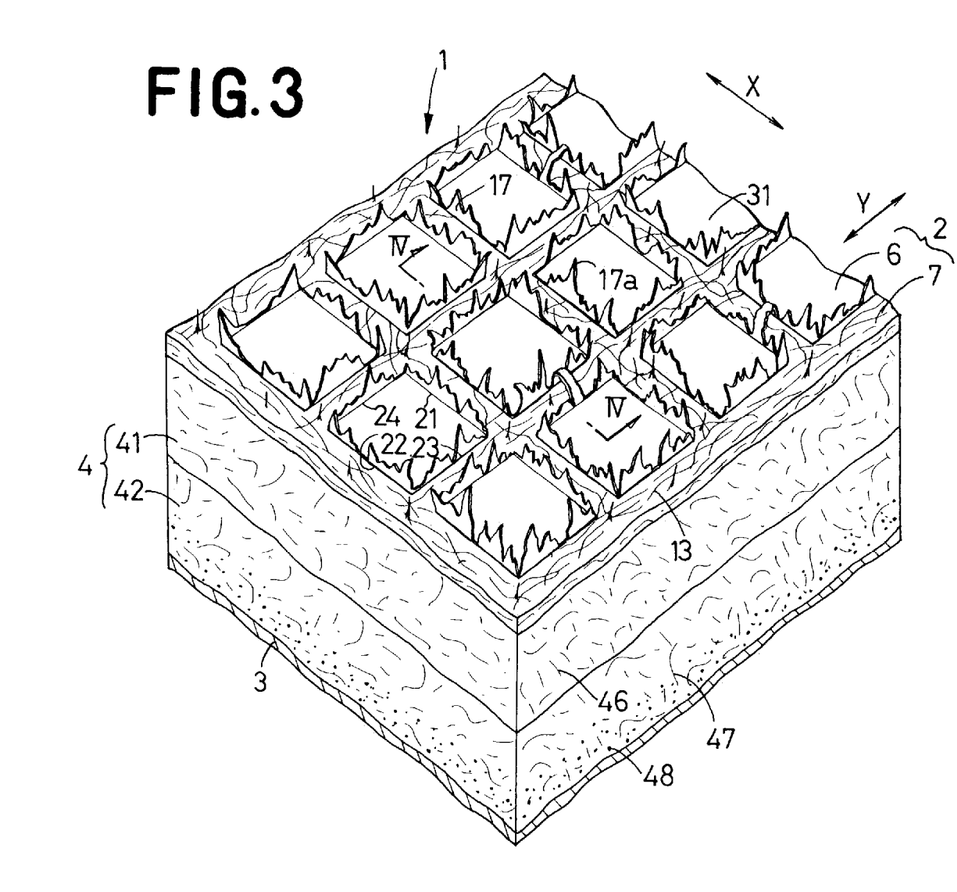
FIG. 3 is a perspective view showing a part of FIG. 1 in an enlarged scale.
Figure 4:
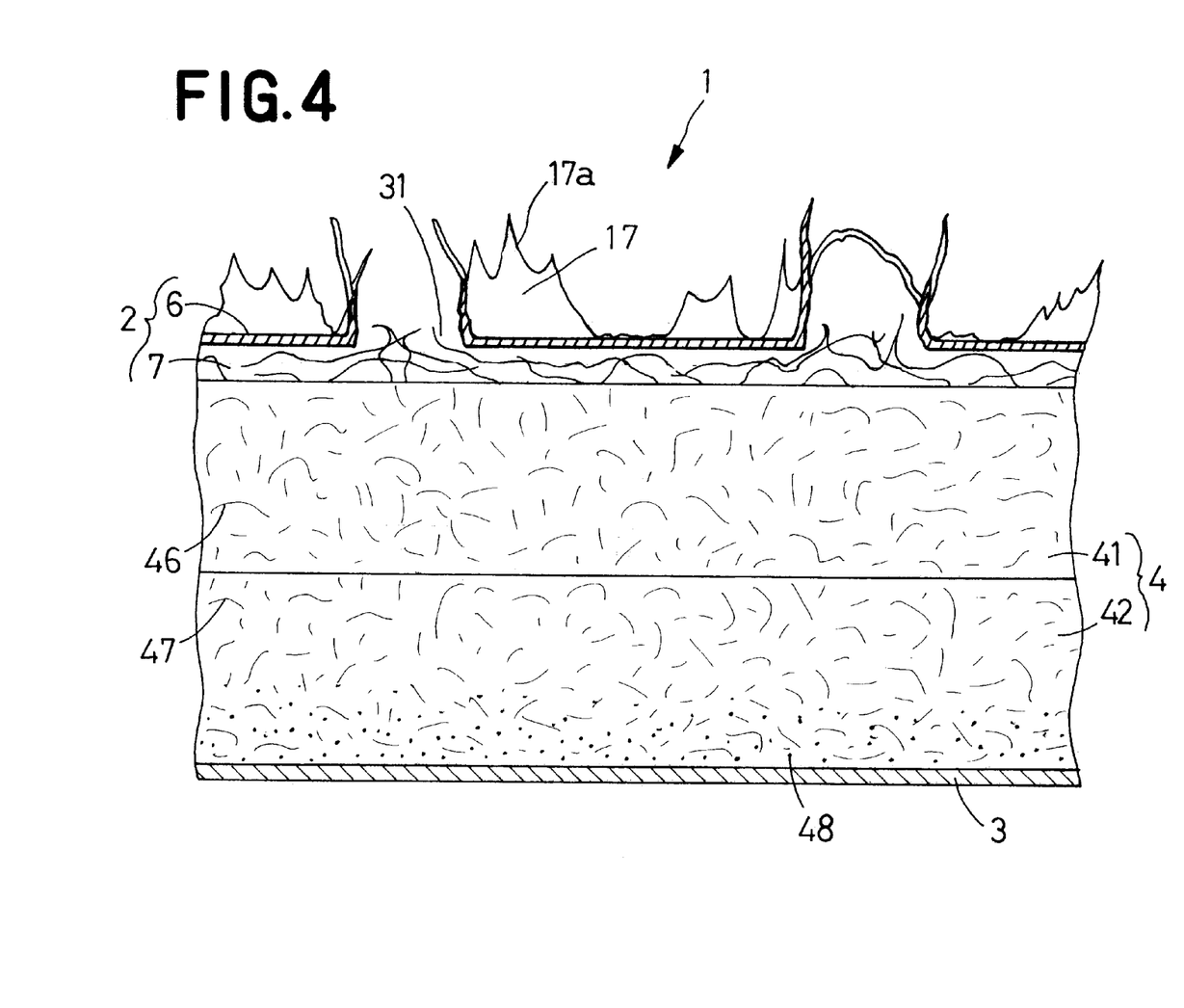
FIG. 4 is a sectional view taken along a line IV—IV in FIG. 3.

FIG. 2 is a sectional view taken along a line II—II in FIG. 1, FIG. 3 a perspective view showing a part of FIG. 1 in an enlarged scale and FIG. 4 a sectional view taken along a line IV—IV in FIG. 3. The film layer sections 6 distributed over the entire area of the topsheet 2 are obtained by high pressure columnar water stream treatment of hydrophobic or weakly hydrophilic thermoplastic sheet material in the manner as disclosed in Japanese Patent Application Publication No. 1999-217453A. Each of the film layer sections 6 has a thickness of 0.05~1 mm and is formed along its peripheral edge with rising portion having a thickness similar to or less than the thickness of the flat film layer section 6. A liquid-pervious opening 31 is formed between each pair of the adjacent film layer sections 6, 6.

The fibrous assembly layer 7 comprises hydrophobic or weakly hydrophilic thermoplastic synthetic component fibers 13 having a fineness of 0.5~20 dtex and a basis weight of 6~60 g/m$^2$. The component fibers 13 are mechanically intertwined, welded or adhesively bonded together. Such fibrous assembly layer 7 is preferably formed with a non-woven fabric selected from a group including a spun lace nonwoven fabric, a spun bond nonwoven fabric, a melt bond nonwoven fabric, an air-through nonwoven fabric and a melt blown nonwoven fabric. The fibrous assembly layer 7 is placed upon and compressed together with the backsheet along a peripheral edge of the napkin 1.

The film layer sections 6 are welded or adhesively bonded to the fibrous assembly layer 7. The film layer sections 6 are intermittently arranged in a first direction X of the topsheet 2 as well as in a second direction Y intersecting the first direction X. A space between each pair of the adjacent film layer sections 6, 6 is less than 1 mm in the first direction X as well as in the second direction Y and, in at least one of these two directions X, Y, 0.05 mm or larger. Such space between the adjacent film layer sections 6, 6 defines an opening which allows the fibrous assembly layer 7 to be exposed toward the skin of the napkin wearer. A total area of these openings 31 preferably occupies 3~40% of the surface area of the topsheet 2. While a shape of the film layer section 6 is not specified, if the shape is quadrilateral as in the illustrated embodiment, first and second sides 21,22 extending in parallel to each other in the first direction X as well as third and fourth sides 23, 24 extending in parallel to each other in the second direction Y are preferably in a range of 0.1~5 mm and crossing angles of these sides 21~24 are preferably in a range of 20~160°.

The rising portion 17 formed along the peripheral edge of the film layer section 6 is of the same material as the plastic sheet material of the film layer section 6 and, more specifically, the rising portion 17 corresponds to the portion of the plastic sheet material fibrillated under the high pressure columnar water streams. Upper edge 17a of the rising portion 17 undulates along the first~fourth sides 21~24 so that the maximum height of the rising portion 17 as measured from the upper surface of the film layer section 6 to its upper edge 17a is 1.5 mm and the minimum height, i.e., the height of the rising portion 17 defining a trough bottom of the undulation of the rising portion 17 and having its upper edge coinciding with the upper surface of the film layer section 6 is 0 mm. In the vicinity of the rising portion 17 having the minimum height, the film layer section 6 is continuous to the fibrous assembly layer 7 exposed in the opening 31. The topsheet 2 constructed in this manner has a Klemm's water absorbency lower than 10 mm as measured in accordance with prescription of JIS P 8141. The topsheet 2 preferably has a breathability of 5~700 cm$^3$/cm$^2$·sec as measured in accordance with prescription of JIS L 1096 and a water-resistance of 0~200 mm as measured in accordance with prescription of JIS L 1092.

In the core 4, the concealing layer 41 contains hydrophilic fibers 46 and has a Klemm's water absorbency lower than 35 mm and higher than the Klemms water absorbency of the topsheet 2 by 15 mm or more. Such concealing layer 41 preferably has a basis weight of 20~50 g/m$^2$ and a density lower than 0.05 g/cm$^3$ which is higher than the density of the fibrous assembly layer 7. The core 4 may be formed, for example, with fluff pulp, a mixture of fluff pulp and thermoplastic synthetic fiber, or thermoplastic synthetic fiber treated to make it rather hydrophilic. The concealing layer 41 may be covered with tissue paper, and bonded to the fibrous assembly layer 7 by means of hot melt adhesive intermittently applied thereto. The liquid holding layer 42 also contains hydrophilic fibers 47 and has a Klemms water absorbency of at least 35 mm and higher than the Klemm's water absorbency of the concealing layer 41 by 15 mm or more. The liquid holding layer 42 is formed with fluff pulp or a mixture of fluff pulp and high absorption polymer grains 48 with a basis weight of, for example, 50~500 g/m$^2$ and a density of 0.05~0.30 g/cm$^3$. The hydrophilic fiber 47 may be fluff pulp, rayon fiber or thermoplastic synthetic fiber treated to make it rather hydrophilic. It is possible to mix the hydrophilic fiber 47 with hydrophobic thermoplastic synthetic fiber up to 20% by weight. The liquid holding layer 42 is provided with a density higher than the density of the concealing layer 41 and, if desired, mixed with an appropriate quantity of highly hydrophilic fiber 47 to ensure that the liquid holding layer 42 may have a water absorbency higher than that of the concealing layer 41 by at least 15 mm. If desired, the liquid holding layer 42 is covered with tissue paper separately or together with the concealing layer 41.

With the sanitary napkin 1 according to such embodiment, menstrual discharge flows through the openings 31 of the topsheet 2 into the fibrous assembly layer 7, then permeates the concealing layer 41 and the liquid holding layer 42, these layers have the Klemm's water absorbency progressively increasing in this order. On the film layer sections 6 of the topsheet 2, menstrual discharge flows through troughs defined between respective pairs of the adjacent individual rising portions 17, 17 into the openings 31. The napkin 1 according to this embodiment allows the topsheet 2 to offer the wearer a dried touch before and after absorption of menstrual discharge without causing a stuffiness even though the film layer sections 6 and the rising portion 17 are hydrophobic. This is because the appropriate gradient of the Klemm's water absorbency enables menstrual discharge to be rapid absorbed by the core 4. The film layer sections 6 of the topsheet 2 are particularly advantageous in that these sections 6 can offer the wearer a dried cloth-like touch and the fibrous assembly layer 7 is particularly advantageous in that this layer 7 can maintain the film layer sections 6 in close contact with the core 4 and thereby can reliably guide menstrual discharge from the openings 31 into the liquid holding layer 42. The concealing layer 41 of the core 4 functions to conceal menstrual discharge absorbed by the liquid holding layer 42 so that the wearer is relieved of somewhat uncomfortable feeling for every disposal of the used napkin. Once menstrual discharge has been absorbed by the high absorption polymer grains 48, there is no anxiety that the menstrual discharge might flow back toward the wearer's skin even if a body weight of the wearer is exerted on the napkin 1. It is possible to arrange each of these concealing layer 41 and liquid holding layer 42 in two or more layers. In such layered structure, the Klemm's water absorbency is preferably adjusted to increase progressively from the uppermost layer to the lowermost layer.

Figure 5:
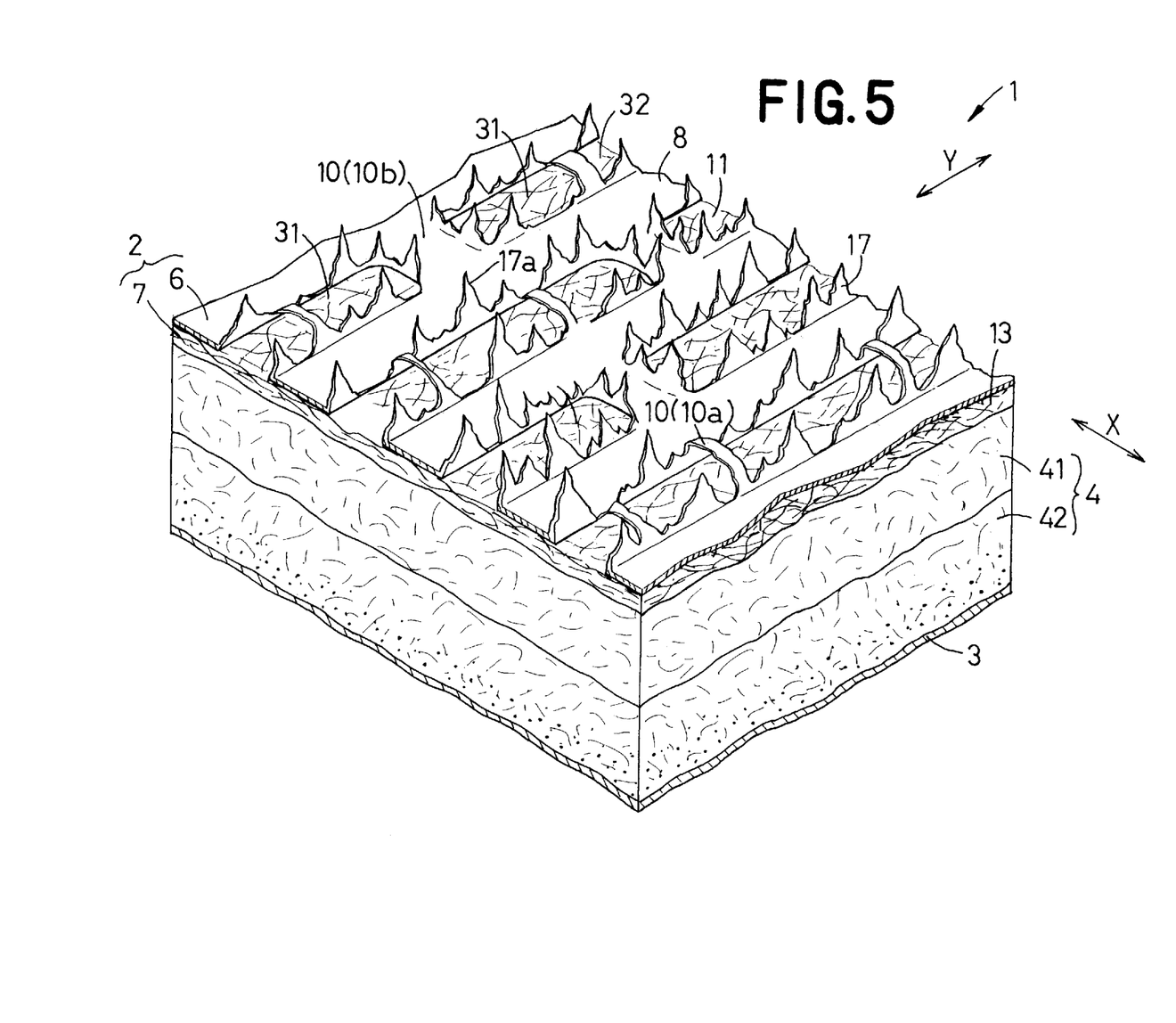
FIG. 5 is a view similar to FIG. 3 but showing another embodiment of this invention.

FIG. 5 a view similar to FIG. 3 but showing another embodiment of this invention. The topsheet 2 of this napkin 1 is formed with the flexible sheet of prior art as shown in FIG. 9. This topsheet 2 has a plurality of film layer sections 6 extending in parallel one to another in the second direction Y, a plurality of opening arrays 32 extending in parallel one to another in the second direction Y, each of the arrays 32 comprising a plurality of openings 31, and the fibrous assembly layer 7 welded or adhesively bonded to the lower surface of the film layer sections 6 and immediately underlying the openings 31. The peripheral edge of the film layer section 6 defining each of the openings 31 is formed with the rising portion 17 extending upward and the upper edge 17a of the rising portion 17 undulates in the second direction Y. Each pair of the film layer sections 6, 6 being adjacent in the first direction X are connected to each other by a bridge-like portion 10 lying between each pair of the openings 31 being adjacent in the second direction Y. The bridge-like portion 10 is classified into a curved one 10a as shown and a flat one 10b. The rising portion 17 may be formed along edges of such bridge-like portion 10 also. The opening 31 preferably has a width of 0.05~1 mm as measured in the first direction X and a length in the second direction Y corresponding to at least 1.5 times the width. A total area of these openings occupies 10~40% of the surface area of the topsheet 2. Component fibers 13 of the fibrous assembly layer 7 partially extend upward through these openings 31. The other characteristics of the film layer sections 6 as well as the fibrous assembly layer 7 closely contiguous to the lower surface of the film layer sections 6 are similar to those in the topsheet 2 shown by FIG. 3. The napkin 1 including such topsheet 2 allows menstrual discharge to flow on the film layer sections 6 in the second direction Y quickly to longitudinally opposite ends of the napkin 1. At these longitudinally opposite ends of the napkin 1 also, menstrual discharge can be effectively absorbed by the core 4. In other words, substantially entire length of the napkin 1 can be used to absorb menstrual discharge.

Figure 6:
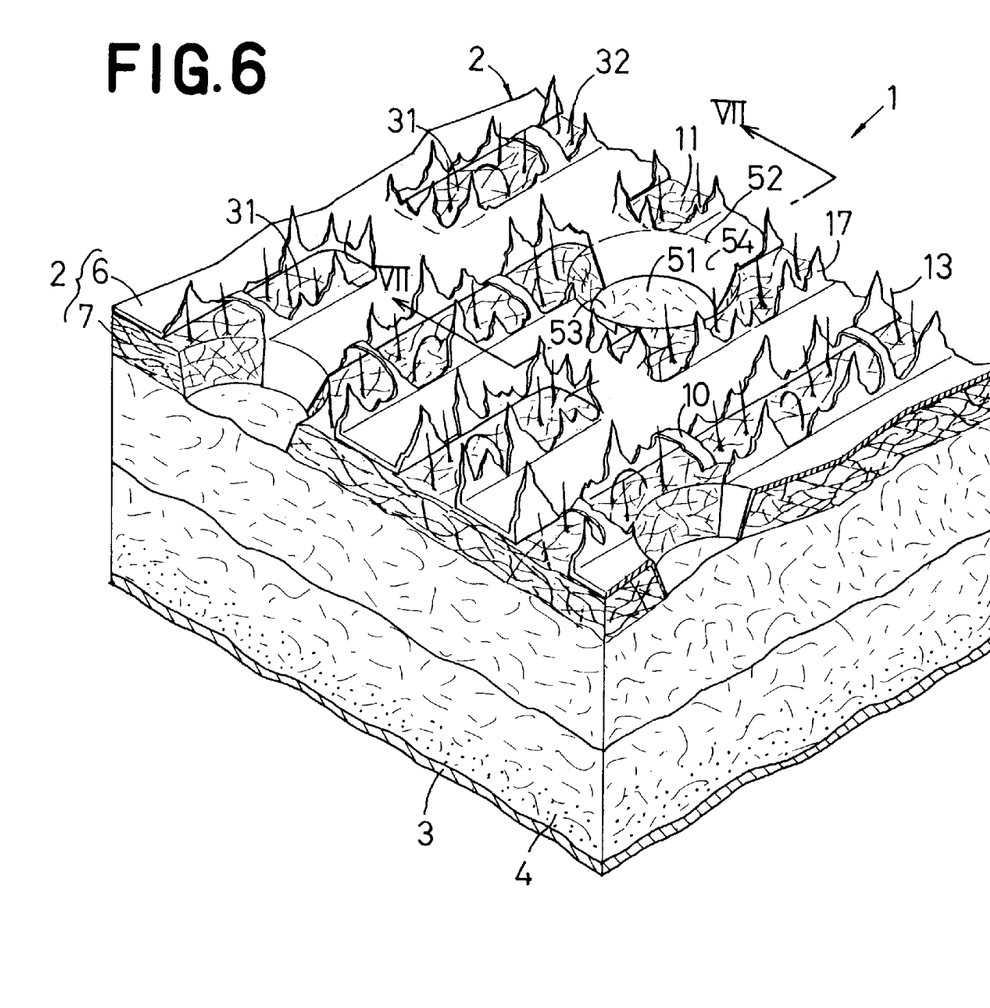
FIG. 6 is a view similar to FIG. 5 but showing another embodiment of this invention.
Figure 7:
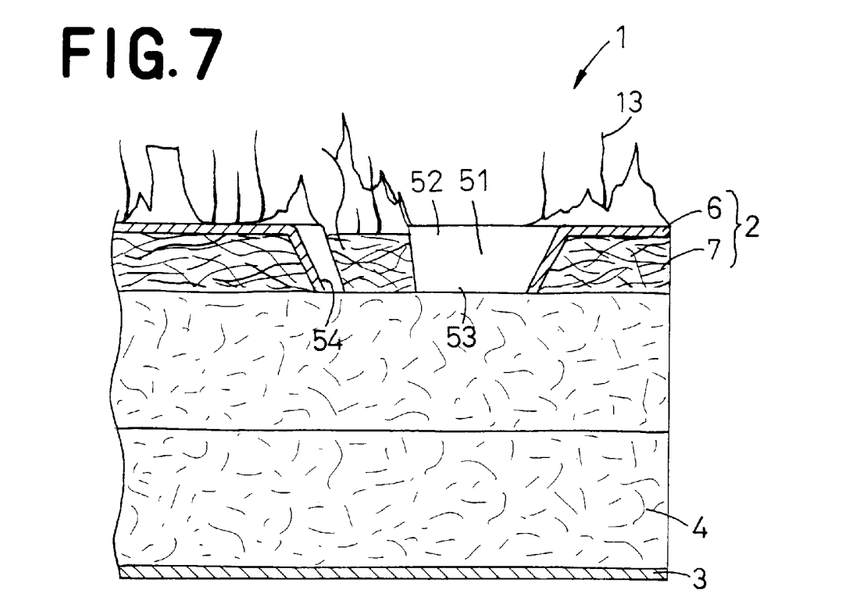
FIG. 7 is a sectional view taken along a line VII—VII in FIG. 6.

FIG. 6 is a view similar to FIG. 5 but showing another embodiment of this invention and FIG. 7 is a sectional view taken along a line VII—VII in FIG. 6. According to this embodiment, the topsheet 2 of the napkin 1 is formed with a plurality of tubular passages 51 extending through the topsheet 2 from its upper surface to its lower surface. Each of the tubular passages 51 has an upper opening 52, a lower opening 53 and a tube wall 54 extending between these two openings 52, 53. The upper and lower openings 52, 53 preferably have a diaper of 0.1~5 mm, more preferably 1.5~5 mm on the upper and lower surfaces of the topsheet 2, respectively, so that a total area of the upper openings 52 may preferably occupy 1~70%, more preferably 5~50% of the upper surface of the topsheet 2. The tube wall 54 is tapered downward at an angle of 0~70% with respect to the vertical. Within such range of tapering degree, the lower opening 53 is preferably dimensioned to be smaller than the upper opening 52. The lower opening 53 immediately overlies the upper surface of the absorbent core 4.

Figure 8:
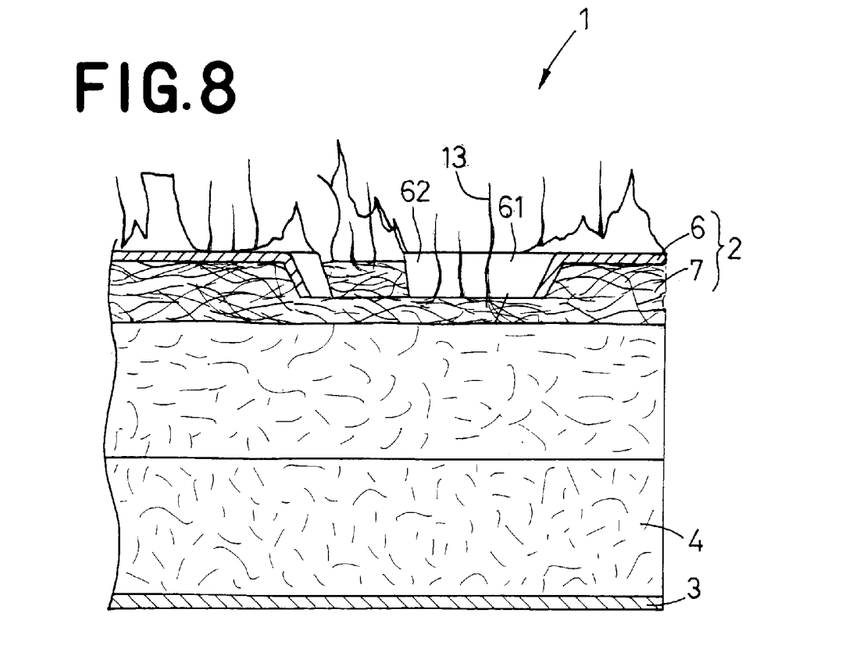
FIG. 8 is a view similar to FIG. 6 but showing still another embodiment of this invention.

FIG. 8 is a view similar to FIG. 7 but showing still another preferred embodiment of this invention. In the case of the topsheet 2 according to this embodiment, tubular depressions 61 extend from the upper surface of the topsheet 2 toward the lower surface of the topsheet 2 and terminate in the interior of the fibrous assembly layer 7. The component fibers 13 of the fibrous assembly layer 7 partially extend upward. These component fibers 13 extend further upward through upper openings 62 of the respective depressions 61 and contribute to a soft touch of the topsheet 2. With the component fibers 13 of weakly hydrophilic nature, body fluids can be smoothly guided to the level below the respective depressions 61 under capillary action. It should be understood that these depressions 61 may be provided in combination with the tubular passages 51 as shown in FIGS. 6 and 7.

While this invention has been described with respect to the napkin 1 as one of typical embodiments, this invention can be implemented also in the form of the other disposable body fluid absorbent wearing article such as a disposable diaper or a urine absorbent pad.

In the disposable body fluid absorbent wearing article according to this invention, the topsheet has the fibrillated portion contributing to a cloth-like touch of the article and comprises the plastic film layer sections defining the liquid-pervious openings and the fibrous assembly layer integrated with the plastic film layer sections. The topsheet is closely contiguous to the absorbent core and the Klemm's water absorbency progressively increases from the topsheet toward the liquid holding layer of the core. Consequently, this wearing article allows body fluids to be rapidly absorbed by the core even though the film layer sections of the topsheet are hydrophobic or weakly hydrophilic so that a dried touch may be obtained.

What is claimed is:

1. A disposable body fluid absorbent wearing article comprising:
    a liquid-pervious topsheet;
    a liquid-impervious backsheet; and
    a liquid-absorbent core disposed between said liquid-pervious topsheet and said liquid-impervious backsheet, said liquid-pervious topsheet comprising:
        a plurality of plastic film layer sections each having upper and lower surfaces and a thickness of from about 0.001 to about 0.05 mm;
        openings defined between respective pairs of adjacent one of said plastic film layer sections; and
        a first fibrous layer bonded to the lower surfaces of said plastic film layer sections and immediately underlying said openings,
    said liquid-pervious topsheet having a Klemm's water absorbency lower than 10 mm,
    each of said openings having a width of from about 0.05 to about 1 mm so that a total open area thereof occupies from about 3 to about 4% of a surface area of said topsheet,
    edges of said plastic film layer sections defining said openings being partially fibrillated so as to form rising portions having a maximum height of 1.5 mm, said first fibrous layer having component fiber having a fineness of from about 0.5 to about 20 dtex and a basis weight of from about 5 to about 60 g/m$^2$,
    said liquid-absorbent core having a second fibrous layer being closely contiguous to a lower surface of said first fibrous layer and a third fibrous layer being closely contiguous to a lower surface of said second fibrous layer, said second fibrous layer having a Klemm's water absorbency lower than 35 mm but higher than a Klemm's water absorbency of said liquid-pervious topsheet by 15 mm or more and said third fibrous layer having a Klemm's water absorbency of at least 35 mm but higher than said Klemm's water absorbency of said second fibrous layer by 15 mm or more.

2. The article according to claim 1, wherein each of said openings has a width of from about 0.05 to about 1 mm and a length corresponding to at least 1.5 times said width.

3. The article according to claim 1, further comprising a plurality of tubular passages that extend through said liquid-pervious topsheet from an upper surface thereof to its lower surface, said tubular passages having tube walls comprising upper and lower openings, each of said upper and lower openings having a diameter of from about 0.1 to about 5 mm.

4. The article according to claim 1, wherein said liquid-pervious topsheet comprises a plurality of depressions extending from an upper surface thereof toward the lower surface thereof, said depressions terminating within an interior of said first fibrous layer, each of said depressions having an opening having a diameter of from about 0.1 to about 5 mm, on the upper surface of the liquid-pervious topsheet.

5. The article according to claim 1, wherein one of said second and third fibrous layers comprises a plurality of fibrous layers and has a Klemm's water absorbency progressively increasing from an uppermost layer to a lowermost layer.

6. The article according to claim 1, wherein the edges of said plastic film layer sections are firmed with a plurality of fibrillated portions so that said plastic film layer sections are contiguous to the portions of said first fibrous layer exposed through said openings between respective pairs of adjacent ones of said fibrillated portions.

7. The article according to claim 1, wherein said second fibrous layer contains hydrophilic fibers and has a basis weight of from about 20 to about 50 $g/m^2$ and a density lower than 0.05 $g/cm^2$ but higher than the density of said first fibrous layer.

8. The article according to claim 7, wherein said hydrophilic fiber comprises fluff pulp.

9. The article according to claim 1, wherein said third fibrous layer contains hydrophilic fibers and has a basis weight of from about 50 to about 500 $g/m^2$ and a density of from about 0.05 to about 0.30 $g/cm^3$.

10. The article according to claim 1, wherein said third fibrous layer contains from about 5 to about 50% by weight of high absorption polymer grains.

* * * * *

(12) EX PARTE REEXAMINATION CERTIFICATE (5461st)
United States Patent
Takai et al.

(10) Number: US 6,770,795 C1
(45) Certificate Issued: Jul. 25, 2006

(54) DISPOSABLE BODY FLUID ABSORBENT WEARING ARTICLE

(75) Inventors: Hisashi Takai, Kagawa-ken (JP); Koichi Yamaki, Kagawa-ken (JP); Miou Suzuki, Kagawa-ken (JP)

(73) Assignee: Uni-Charm Corporation, Kawanoe (JP)

Reexamination Request:
No. 90/007,457, Mar. 9, 2005

Reexamination Certificate for:
Patent No.: 6,770,795
Issued: Aug. 3, 2004
Appl. No.: 09/940,930
Filed: Aug. 28, 2001

(30) Foreign Application Priority Data
Aug. 28, 2000 (JP) ........................................ 2000-257639

(51) Int. Cl.
*A61F 13/15* (2006.01)
*A61F 13/20* (2006.01)

(52) U.S. Cl. ........................................ 604/378; 604/380
(58) Field of Classification Search .................. 604/378, 604/382, 380, 385.01, 379, 367; 428/131, 428/137, 138
See application file for complete search history.

(56) References Cited

U.S. PATENT DOCUMENTS 5,236,427 A * 8/1993 Hamajima et al. .......... 604/378
2001/0039406 A1 * 11/2001 Hamajima et al. .......... 604/378

FOREIGN PATENT DOCUMENTS

EP 0719531 A1 3/1996
EP 1025826 A2 9/2000

OTHER PUBLICATIONS

Reed, C.M. and Wilson N., The fundamentals of absorbency of fibres, textile structures and polymers, I: the rate of rise of a liquid in glass capillaries, J. Phys. D: Appl. Phys., vol. 26, No. 9 (Sep. 14, 1993), pp. 1378–1381.*

* cited by examiner

*Primary Examiner*—Sara Clarke (57) ABSTRACT

A disposable body fluid absorbent wearing article includes a liquid-pervious topsheet including plastic film layer sections, liquid-pervious openings and a first fibrous layer bonded to the lower surface of the film layer sections. A second fibrous layer forming a liquid-absorbent core is contiguous to the lower surface of a first fibrous layer and a third fibrous layer is contiguous to the lower surface of the second fibrous layer. The wearing article is constructed so that its Klemm's water absorbency may progressively increase in the order of the first fibrous layer, the second fibrous layer and the third fibrous layer.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–10 is confirmed.

* * * * *